(12) United States Patent
Kressierer/Huber et al.

(10) Patent No.: US 7,637,288 B2
(45) Date of Patent: Dec. 29, 2009

(54) RESPIRATORY GAS HOSE SYSTEM FOR SUPPLYING A RESPIRATORY GAS

(75) Inventors: Petra Kressierer/Huber, Erding (DE); Bernd Christoph Lang, Gräfelfing (DE); Achim Biener, Munich (DE); Dieter Heidmann, Berg (DE)

(73) Assignee: MAP Medizin-Technologie GmbH, Martinsried (DE)

( * ) Notice: Subject to any disclaimer, the term of this patent is extended or adjusted under 35 U.S.C. 154(b) by 0 days.

(21) Appl. No.: 11/417,234

(22) Filed: May 4, 2006

(65) Prior Publication Data

US 2006/0249212 A1    Nov. 9, 2006

Related U.S. Application Data

(63) Continuation of application No. 10/204,014, filed as application No. PCT/EP01/01751 on Feb. 16, 2001, now Pat. No. 7,086,422.

(30) Foreign Application Priority Data

Feb. 18, 2000    (DE) .................... 100 07 506

(51) Int. Cl.
*F16L 9/14*    (2006.01)
(52) U.S. Cl. .................. 138/149; 138/109; 138/33; 138/167; 138/168; 128/207.14
(58) Field of Classification Search .............. 138/149, 138/33, 167, 168; 128/207.14, 205.12
See application file for complete search history.

(56) References Cited

U.S. PATENT DOCUMENTS

| | | | |
|---|---|---|---|
| 2,516,864 A | | 8/1950 | Gilmore et al. |
| 3,034,085 A | * | 5/1962 | Pauler et. al. ............... 439/191 |
| 3,314,039 A | | 4/1967 | Opper |
| 3,379,218 A | * | 4/1968 | Conde ........................ 138/99 |
| 3,764,779 A | * | 10/1973 | Kadoya et al. .............. 219/201 |
| 3,928,715 A | | 12/1975 | Holden |
| 4,038,519 A | * | 7/1977 | Foucras ...................... 392/472 |
| 4,042,803 A | | 8/1977 | Bickford |
| 4,138,178 A | * | 2/1979 | Miller et al. ................ 439/192 |
| 4,162,370 A | * | 7/1979 | Dunn et al. ................... 174/47 |
| 4,279,255 A | | 7/1981 | Hoffman |
| 4,327,723 A | | 5/1982 | Frankhouser |
| 4,400,420 A | | 8/1983 | Bakken et al. |

(Continued)

FOREIGN PATENT DOCUMENTS

DE    19725875    12/1998

(Continued)

OTHER PUBLICATIONS

ResCare Limited et al., Sullivan® Tubing Wrap "User Instructions", 16805/0, 94 08, (May 1996), 1 pg.

(Continued)

*Primary Examiner*—James F Hook
(74) *Attorney, Agent, or Firm*—Nixon & Vanderhye P.C.

(57) ABSTRACT

A respiratory gas hose system for supplying a respiratory gas, particularly for use in the framework of CPAP therapy, includes a flexible hose line and a flexible sheathing body which surrounds the flexible hose line and extends along the flexible hose line. This results in considerably improved therapy comfort.

17 Claims, 5 Drawing Sheets

U.S. PATENT DOCUMENTS

| | | | | |
|---|---|---|---|---|
| 4,553,023 | A | * | 11/1985 | Jameson et al. ............. 392/472 |
| 4,639,055 | A | * | 1/1987 | Keane ....................... 439/192 |
| 4,682,010 | A | * | 7/1987 | Drapeau et al. ............ 392/488 |
| 4,736,088 | A | | 4/1988 | Bart |
| 4,815,769 | A | | 3/1989 | Hopperdietzel |
| 4,920,235 | A | | 4/1990 | Yamaguchi |
| 4,930,543 | A | | 6/1990 | Zuiches |
| 4,944,987 | A | * | 7/1990 | Cordia et al. ............... 428/192 |
| 4,967,744 | A | | 11/1990 | Chua |
| 5,112,661 | A | | 5/1992 | Pendergraft et al. |
| 5,226,456 | A | * | 7/1993 | Semak ....................... 138/107 |
| 5,236,765 | A | * | 8/1993 | Cordia et al. ............... 428/192 |
| 5,377,670 | A | | 1/1995 | Smith |
| 5,387,117 | A | | 2/1995 | Moyher et al. |
| 5,392,770 | A | | 2/1995 | Clawson et al. |
| 5,522,433 | A | * | 6/1996 | Nygaard .................... 138/149 |
| 5,537,996 | A | | 7/1996 | McPhee |
| 5,600,752 | A | | 2/1997 | Lopatinsky |
| 5,632,919 | A | | 5/1997 | MacCracken et al. |
| 5,640,951 | A | | 6/1997 | Huddart et al. |
| 5,651,161 | A | * | 7/1997 | Asta ........................... 15/325 |
| 5,715,815 | A | | 2/1998 | Lorenzen et al. |
| 5,791,377 | A | | 8/1998 | LaRochelle |
| 5,883,363 | A | * | 3/1999 | Motoyoshi et al. .......... 219/529 |
| 5,901,705 | A | * | 5/1999 | Leagre .................. 128/207.14 |
| 5,901,756 | A | * | 5/1999 | Goodrich .................... 138/167 |
| 5,983,896 | A | * | 11/1999 | Fukunaga et al. ...... 128/207.14 |
| 6,032,697 | A | | 3/2000 | Kennedy |
| 6,078,730 | A | * | 6/2000 | Huddart et al. ............. 392/480 |
| 6,109,259 | A | * | 8/2000 | Fitzgerald ............... 128/200.26 |
| 6,536,428 | B1 | * | 3/2003 | Smith et al. ............ 128/203.17 |
| 6,641,304 | B1 | * | 11/2003 | Ang et al. .................... 374/147 |
| 6,738,566 | B2 | * | 5/2004 | Pagnella ..................... 392/472 |
| 6,769,431 | B2 | * | 8/2004 | Smith et al. ............ 128/203.16 |
| 6,953,354 | B2 | * | 10/2005 | Edirisuriya et al. ......... 439/191 |
| 7,086,422 | B2 | * | 8/2006 | Huber et al. ................. 138/149 |
| 2003/0007789 | A1 | * | 1/2003 | Pagnella ..................... 392/472 |
| 2003/0059213 | A1 | * | 3/2003 | Mackie et al. .............. 392/480 |
| 2004/0065335 | A1 | | 4/2004 | Huber et al. |
| 2004/0103949 | A1 | | 6/2004 | Rickards |
| 2004/0118401 | A1 | * | 6/2004 | Smith et al. ............ 128/204.17 |
| 2004/0200536 | A1 | | 10/2004 | Strasser et al. |
| 2004/0261879 | A1 | | 12/2004 | Maida |

FOREIGN PATENT DOCUMENTS

| | | |
|---|---|---|
| DE | 20018593 | 1/2001 |
| EP | 061050 A | 10/1994 |
| WO | WO 9826826 | 6/1998 |

OTHER PUBLICATIONS

International Search Report, PCT/EP2001/001751 (Jun. 5, 2001).

* cited by examiner

RESPIRATORY GAS HOSE SYSTEM FOR SUPPLYING A RESPIRATORY GAS

CROSS-REFERENCE TO RELATED APPLICATIONS

This application is a continuation of U.S. application Ser. No. 10/204,014, filed Apr. 17, 2003, allowed, which is the National Phase of International Application PCT/EP01/01751, filed Feb. 16, 2001, which designated the U.S., each of which is incorporated herein by reference in its entirety.

TITLE OF THE INVENTION

The invention relates to a respiratory gas tube arrangement for supplying a respiratory gas to a person.

Such respiratory gas tube arrangements are used in particular in the field of sleep medicine for the treatment of sleep-related respiratory problems. Thus, for example, even a comparatively low positive pressure of the respiratory gas is capable of providing a pneumatic splint for the upper respiratory tract, this making it possible in effective manner to prevent the risk of obstructions of the respiratory passages.

The treatment of sleep-related respiratory problems by the application of continuous positive pressure to the respiratory passages is generally referred to as CPAP therapy. In the known CPAP devices used for this purpose, conventionally a sound-insulated housing is provided with a delivery means, especially a blower, the delivery pressure of which is adjusted, if necessary by means of an electronic control means, to the breathing of the patient. The respiratory gas delivered by the delivery means, usually ambient air, is supplied to the patient through a flexible respiratory gas tube arrangement. Normally used for this purpose are breathing masks which are placed on the nose of the patient without covering the patient's mouth. CPAP therapy has been shown to represent an effective and physiologically well compatible method for the treatment of sleep-related respiratory problems. However, the flexible tube provided for connecting the patient's breathing mask to the CPAP device is often found to be bothersome.

The object of the invention is to create a device for supplying a respiratory gas to a patient, said device being characterized by an increased convenience of use.

The object of the invention is achieved by the respiratory gas tube arrangement indicated in claim 1.

This makes it possible in advantageous manner to avoid direct contact of the tube with the patient and to conceal the tube in a manner advantageous with respect to aesthetic considerations. In especially advantageous manner, the formation of condensation in the tube is also prevented, with the result that, even in the case of high absolute humidity of the respiratory gas, it is not possible for any drops of condensation to form inside the flexible tube.

According to a particularly preferred embodiment of the invention, the flexible sheathing body is made from a soft textile material, especially fleece material.

In advantageous manner, the flexible sheathing body is of such dimensions that the flexible tube is loosely held therein. Preferably, the inside diameter of the flexible sheathing body is at least 1.3 times the outside diameter of the flexible tube. The air cushion formed between the outside wall of the flexible tube and the flexible sheathing body results in a further improvement of convenience of use as well as insulating effect.

It is possible for the flexible sheathing body to be formed of a multi-layered material which only in the outer region comprises a pleasing outer layer selected with respect to aesthetic considerations.

According to a particularly preferred embodiment of the invention, the flexible sheathing body comprises in the region of its ends a closing means by which the end region of the flexible sheathing body can be narrowed—e.g. drawn together—and can be fixed with a comparatively tight fit to the flexible tube. According to a particularly preferred embodiment of the invention, used as a suitable fixing means is a lashing cord which is passed through eyes and/or a hollow seam and which allows the corresponding end of the flexible sheathing body to be drawn together. Alternatively thereto or in combination therewith, it is possible to provide the end region of the flexible sheathing body with a VELCRO™ (hook and loop) fastener means which allows the end of the flexible sheathing body to be suitably narrowed.

The wall thickness of the flexible sheathing body is preferably in the range from 1-7 mm. The material used may be, for example, a solid material (fleece material) or a multi-layered material. In particularly advantageous manner, a flexible textile layer is laminated onto a padding layer, e.g. of foam plastic material.

The flexible sheathing body is preferably in the form of a tube-like body and is slipped onto the flexible tube.

Alternatively, it is also possible for the flexible sheathing body to be formed of a strip material comprising a joining means extending in the longitudinal direction of the strip material. Said joining means is advantageously a VELCRO™ (hook and loop) fastener tape. Alternatively, it is also possible to use zip fasteners, button-hole arrangements or press studs.

In particularly advantageous manner, it is possible, in the region of the CPAP device as well as preferably also in the region of the breathing mask, to provide joining means by which the flexible sheathing body can be reliably fixed. In advantageous manner, said fixing means consist of a hook or pile tape which is fixed, preferably glued or clipped, to the tube in the respective end region (mask or CPAP device).

According to a particularly preferred embodiment of the invention, it is also possible, in the region of the ends of the sheathing body, to provide elastic cuffs by which the sheathing material of the sheathing body is forced onto the tube or end pieces of the tube. For this purpose, it is possible, for example, to provide a rubber band in the end region of the sheathing body, the rubber band preferably being accommodated in a hollow seam.

It is possible in advantageous manner to provide a non-slip, e.g. rubberized, layer in the region of the contact zones of the sheathing body on the tube.

The heat- and sound-insulating effect can in advantageous manner be adjusted to suit the requirements by means of the material characteristics and construction of the sheathing body. An especially great heat-insulating effect is achieved by using two or more layers of fleece material. It is possible to topstitch or quilt the layers of fleece material preferably in connection with covering and lining layers.

At least the outer region of the sheathing body is preferably multi-coloured. Such multi-colouring is achieved preferably by stitching together multi-coloured textile portions, the joining seams simultaneously serving as quilting seams.

It is possible to incorporate a band- or rod-like stiffening insert into the sheathing body, this providing a fitting aid if the sheathing body is in the form of a tube.

If the sheathing body is split longitudinally, it is possible, as an alternative to VELCRO™ (hook and loop) or stud, especially press stud, fasteners, to employ a longitudinal zip fastener. Such longitudinal zip fastener is preferably overlapped such that the structure of the zip fastener is concealed on the outside. It is also possible to provide a magnetic closing means.

According to a particularly preferred embodiment of the invention, a heating means is integrated into the sheathing body. Said heating means may be in the form of an electrical resistance heating means. According to a particularly preferred embodiment, the heating means comprises a low-voltage heating foil, the power consumption characteristics of said heating foil being so selected that the heating foil is self-regulating and does not exceed a predetermined heating temperature. The heating foil may be sewn into the sheathing body, it preferably being the case that the heat-insulating capacity of the sheathing body outside the heating foil is greater than in the region between heating foil and tube. Alternatively, it is also possible for the tube to be in the form of a heatable respiratory gas tube.

The power supply to the heating means is preferably by means of a low-voltage cable provided with a connector which can be plugged into a corresponding power supply socket of a power supply unit—or preferably into a power supply socket provided on a CPAP device or air humidifier. Such a heatable sheathing body not only reliably prevents condensation, but also allows temperature stabilization of the respiratory gas.

It is possible for insulation means to be provided in the region of the sheathing body in order to shield against heat radiation. Preferably, the inside of the sheathing body adjoining the tube is provided with a metallized, e.g. aluminium-, silver- or gold- vapour-deposited, super-insulating foil.

According to a particularly preferred embodiment of the invention, the sheathing body is provided with at least one—preferably a plurality of—fixing points by which the sheathing body—and thus the entire tube arrangement—can be suspended or fixed in a defined manner with regard to its spatial mobility. Such fixing points may, for example, be in the form of eyes. Preferably, between two and four such eyes are arranged at intervals from each other along the tube.

According to a particularly preferred embodiment of the invention, the sheathing body is so designed that it forms a container section into which the other part of the sheathing body can be inserted. This container section which is integrated into the sheathing body may be in the form of a flat bag or pocket region formed by sewing a flexible layer onto an outside surface of the sheathing body. It is also possible for the majority of the sheathing body to be forced into the inside region of one of its longitudinal end sections. For this purpose, one longitudinal section of the sheathing body is preferably in the form of a bag.

An especially weight-saving embodiment of the sheathing body is achieved in that at least one of the insulating layers is in the form of an air-cushion layer.

According to a special aspect of the present invention, the sheathing body is of such design that its bending characteristics vary as viewed in the longitudinal direction of the sheathing body. Thus, for example, it is possible to provide the near-mask region of the sheathing body with a high degree of flexibility, whereas, in the near-device region, the sheathing body is of stiffer design. The deformation characteristics of the sheathing body can be determined by inserts of articulated and/or bending material.

According to a particularly preferred embodiment of the invention, the sheathing body is provided with an anti-kinking means, for example in the form of spiral or wavy inserts. This makes it possible for the respiratory gas tube, accommodated in the sheathing body, to be of thin-walled design—possibly in the form of a disposable lightweight tube.

According to a particularly preferred embodiment of the invention, the sheathing body may also be longer than the actual tube. This makes it possible for additional functional elements to be covered by the sheathing body. Thus, in connection with the sheathing body it is possible for elements coupled in modular fashion, for example, to the tube to be covered by the sheathing body and for them to be combined to form apparently one single unit.

In particular, it is possible for a pipe- or tube-shaped air humidifier, gas analysis module, gas flow sensor, pressure lock or similar to be coupled in modular fashion to the tube in the vicinity of the mask and for such device to be covered and, if required, insulated by the sheathing body. In this connection, any additional lines of an electrical, optical or pneumatic nature are advantageously covered by the sheathing body.

The sheathing body forms a flexible, preferably heat- and sound-insulating housing component covering and combining the individual modules.

The sheathing body may be provided with a plurality of openings through which lines, for example of a water trap, can be brought out of the sheathing body. Such openings are preferably closable by means of covers.

Further details of the invention will become apparent from the following description, in which reference is made to the appended drawings, in which.

Figure 1:
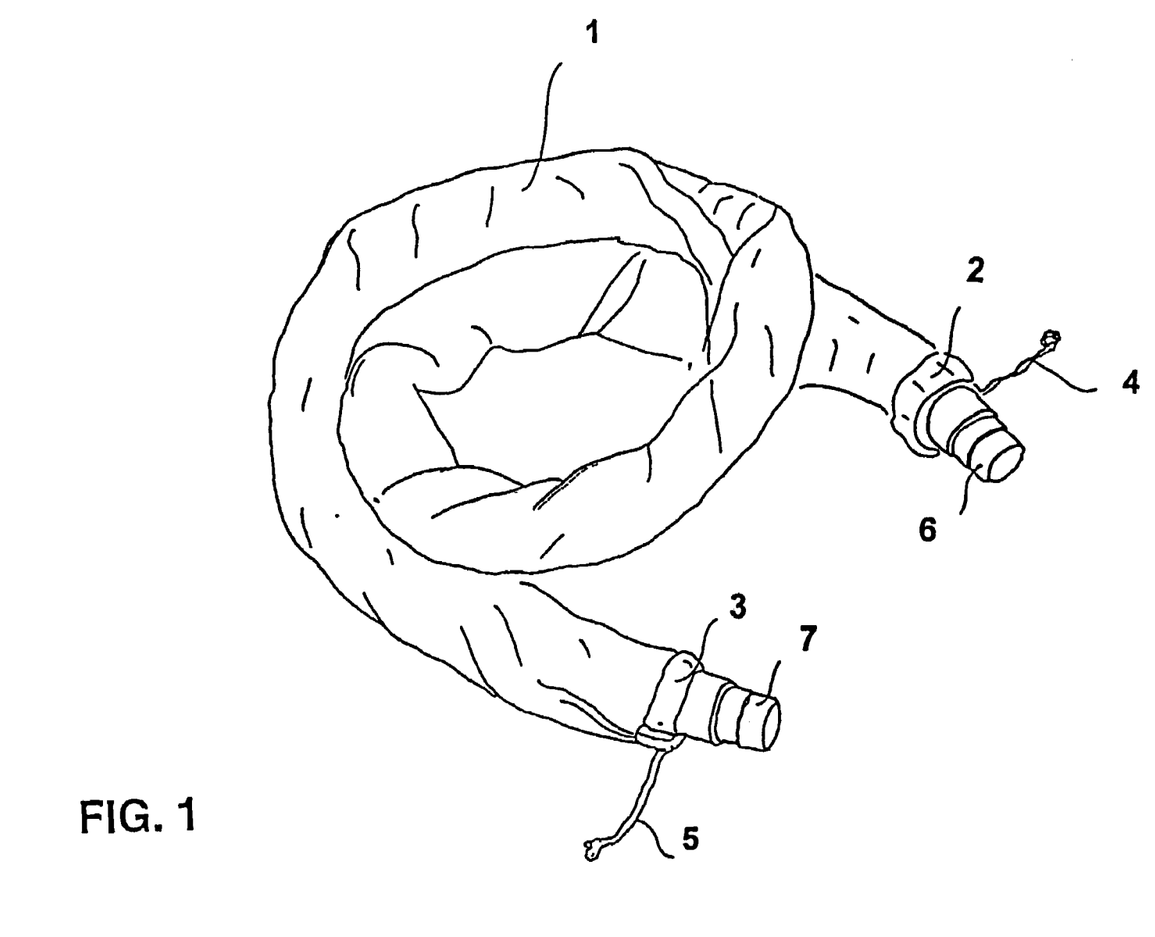
FIG. 1 shows a perspective view of a CPAP respiratory gas tube arrangement, with the sheathing body proposed according to the invention, said sheathing body being made of a soft textile material.

The respiratory gas tube arrangement shown in FIG. 1 comprises a flexible tube (not visible here), made from a spirally reinforced plastic material, and an insulating sheathing body 1, made from an insulating textile material—fleece material, in this case. The sheathing body 1 is formed of a narrow strip of material stitched along one longitudinal seam (overlock seam) to form a tube. In the embodiment shown here, formed in each end region of the sheathing body 1 is a hollow seam 2, 3 through which is passed a cord 4, 5. Through corresponding pulling of the cords 4, 5 it is possible to draw together the end regions of the sheathing body 1, this advantageously fixing the sheathing body 1 to the flexible tube. In order to connect the flexible tube to a CPAP device and to a breathing mask, the respective end regions of the tube are provided with elastomer sockets 6, 7 which can be elastically plugged onto or into correspondingly matching connectors.

The sheathing body 1 is of such dimensions that the flexible tube is more or less loosely held therein. The air cushion formed between the inside surface of the sheathing body 1 and the outside surface of the flexible tube results in improved thermal insulation without increase in weight and additionally provides the respiratory gas tube arrangement with a pleasant cushioning effect.

In order to fix the cords 4, 5 in a corresponding lashing position—as will be explained in detail hereinbelow with reference to FIG. 3—fixing means (not visible here) are preferably provided.

Figure 2A:
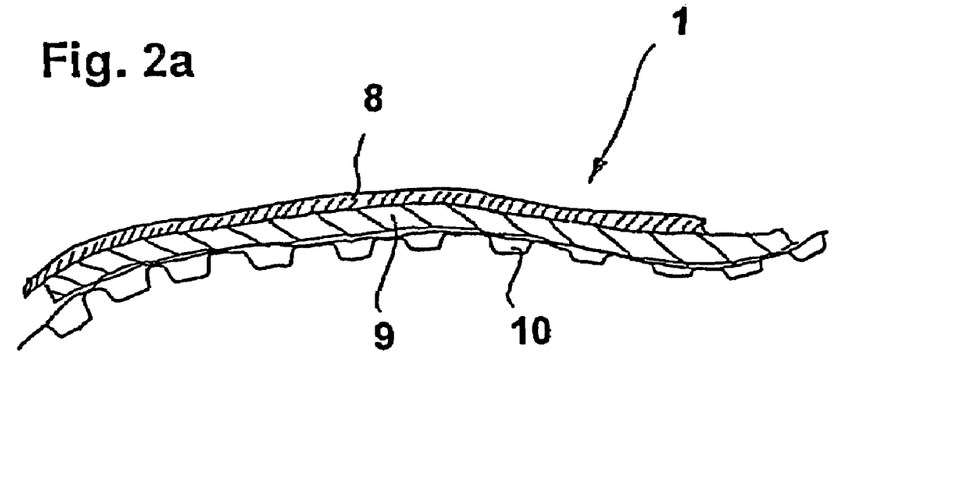
FIG. 2a shows a simplified sectional view through a portion of a multi-layered sheathing body.

As indicated in FIG. 2*a*, the sheathing body 1 is preferably of multi-layered design. Thus, for example, as the uppermost or outer covering layer, a textile covering layer 8, selected with respect to aesthetic considerations, can be laminated onto a cushioning and insulating substrate, which, in this case, consists of a foam plastic layer 9 and a blister film 10. The individual layers may be joined by corresponding glueing, by stitching or, preferably, by hot-laminating. Thus, for example, it is possible to form the insulating foam plastic layer 9 on a foam plastic material whose covering surface welds at a predetermined melting temperature with the outer layer 8 and the blister film 10.

Figure 2B:
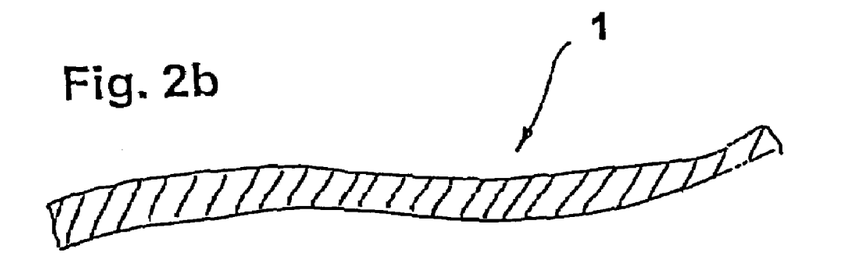
FIG. 2b shows a simplified sectional view through a portion of a single-layered sheathing body.

Alternatively to the multi-layered construction just described, it is also possible for the sheathing body 1 to be formed from a solid material, preferably from a fleece or felt material, as shown in FIG. 2*b*. Preferably, use is made in this connection of materials which permit simple cleaning, preferably washing by boiling.

Figure 2C:
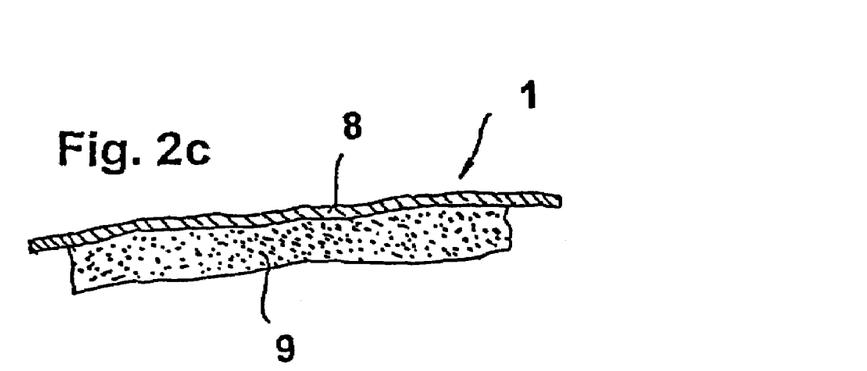
FIG. 2c shows a simplified sectional view through a portion of a two-layered sheathing body with a textile covering layer.

FIG. 2*c* shows a further embodiment of the wall material of the flexible sheathing body 1, which consists in this case of a cushioning and heat-insulating foam plastic layer 9 and a covering layer 8 formed of a decorative fabric material. The joining of the covering layer 8 to the foam plastic material 9 is achieved in this case by means of flame-laminating.

Figure 3:
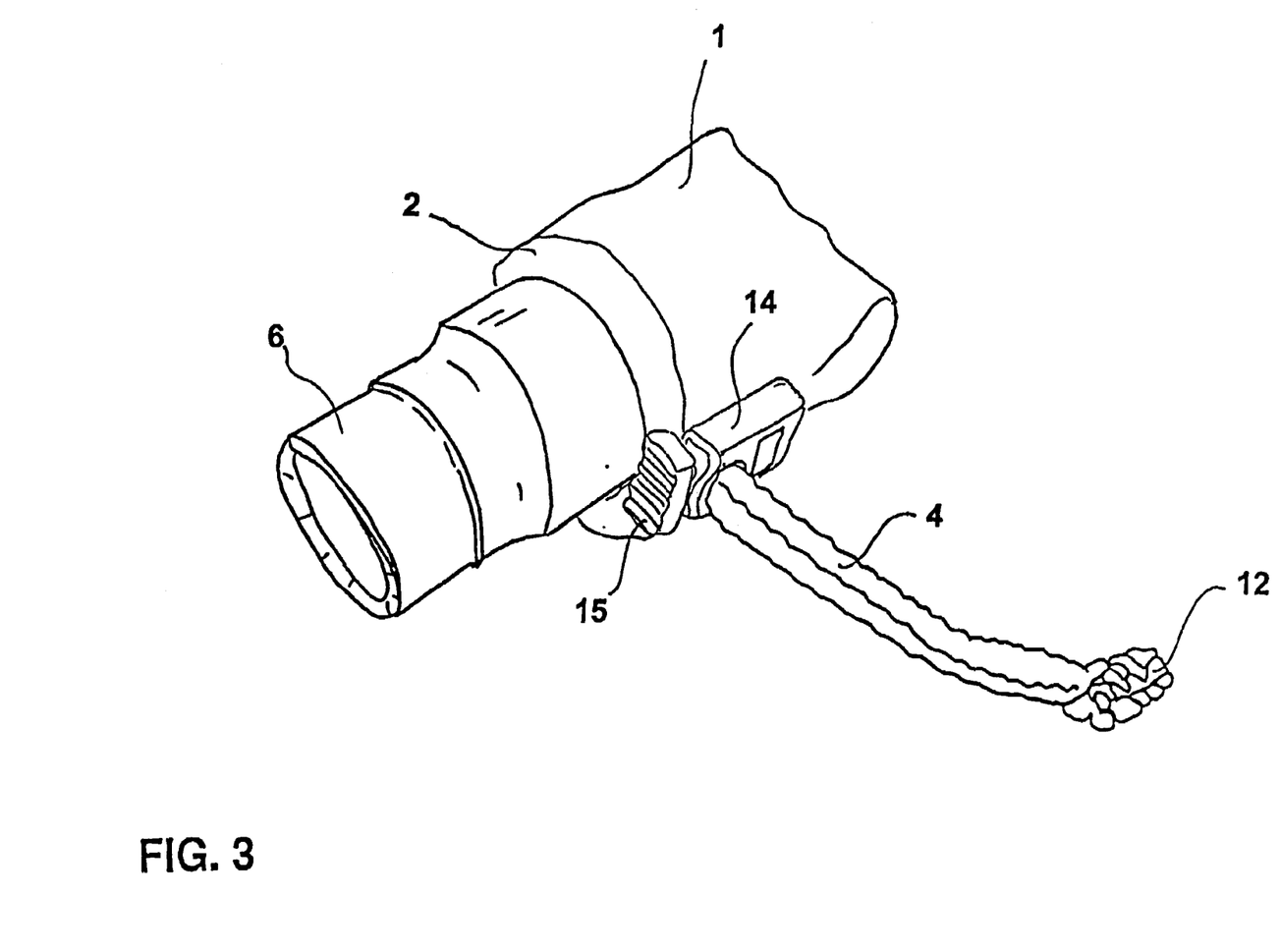
FIG. 3 shows a perspective view for elucidating a fixing means provided in the end region of the flexible sheathing body.

FIG. 3 shows a preferred embodiment of a fixing means for fixing the flexible sheathing body 1 in the end region of the flexible respiratory gas tube. Here, the fixing means comprises a cord 4 which is passed through a hollow seam 2 and which is provided with a knot 12 in the region of each of its protruding ends. Through corresponding pulling on the protruding portion of the cord 4 or on the knot 12 it is possible to draw together the end of the flexible sheathing body 1.

By means of a fixing means 14 it is possible for the cord 4 to be kept in the tightened position. By actuating a releasing means, here in the form of a press button 15, it is possible to loosen the cord 4 and to widen the previously narrowed end of the sheathing body 1. Especially reliable fixing of the sheathing body 1 to the flexible tube can be achieved in that formed in the region of the terminating element, here in the form of the elastomer socket 6, is a structure which is adapted to be brought into engagement with the corresponding end portion of the sheathing body 1. For example, the elastomer socket 6 may be provided with a circumferential groove or circumferential bead to which the suitably drawn-together textile sheathing body 1 can be fixed.

Alternatively to the lashing arrangement shown here, it is also possible to fix the end of the sheathing body 1 to the flexible tube (not shown), for example, by means of a VEL-CRO™ (hook and loop) fastener means or by means of clasps.

Figure 4:
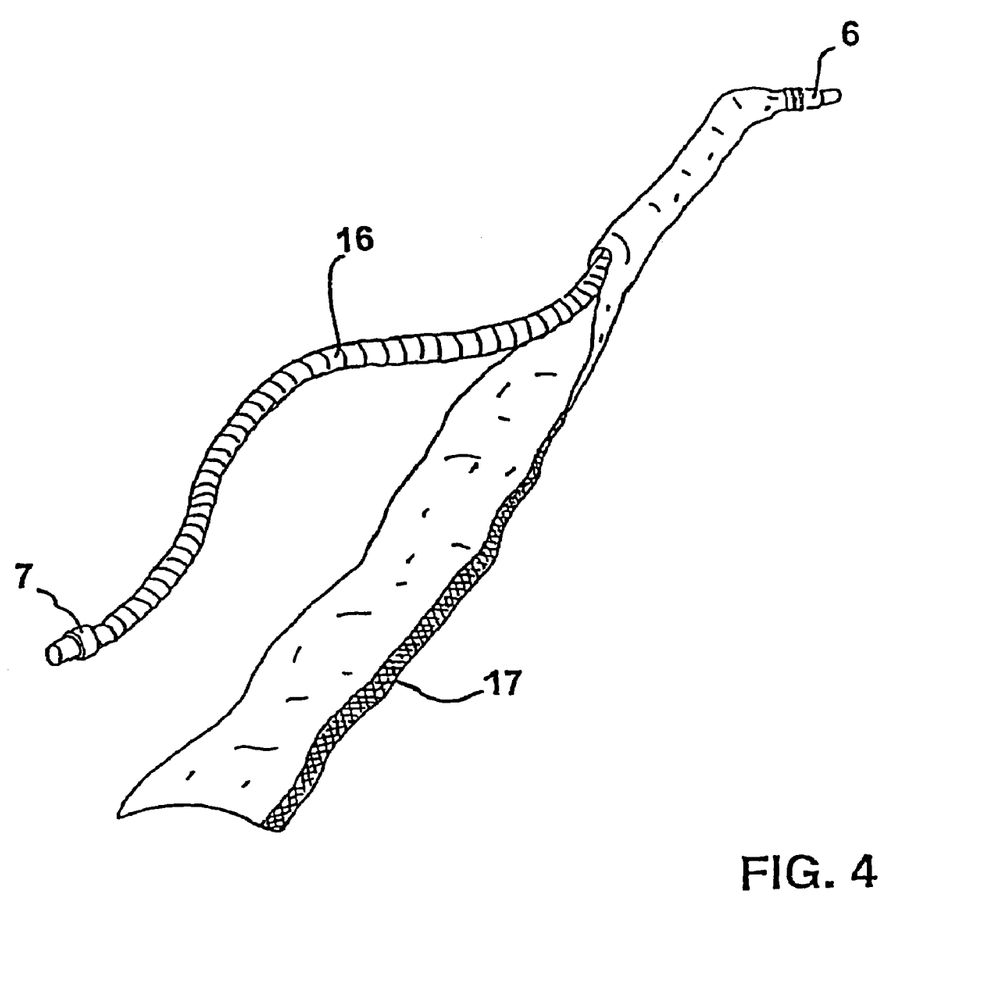
FIG. 4 shows an embodiment of the flexible sheathing body in the form of a longitudinally split body including the joining means extending along the corresponding longitudinal edge, said joining means here being in the form of a VELCRO™ (hook and loop) fastener.

FIG. 4 shows a further embodiment of the respiratory gas tube arrangement which, in this case, comprises a flexible tube 16 provided at its end regions with the elastomer sockets 6, 7. In contrast to the embodiment previously described in connection with FIG. 1, in this case the flexible sheathing body 1 is formed from a flexible textile strip which is guided around the flexible tube 16 and is provided along its longitudinal edge with a joining means 17, with the result that the material strip guided around the tube 16 surrounds the flexible tube 16 likewise in the manner of a tube. In particularly advantageous manner, provided for this purpose in the region of one of the longitudinal edges of the textile material strip is a VELCRO™ (hook and loop) fastener tape.

Figures 5, 6, 7, 8:
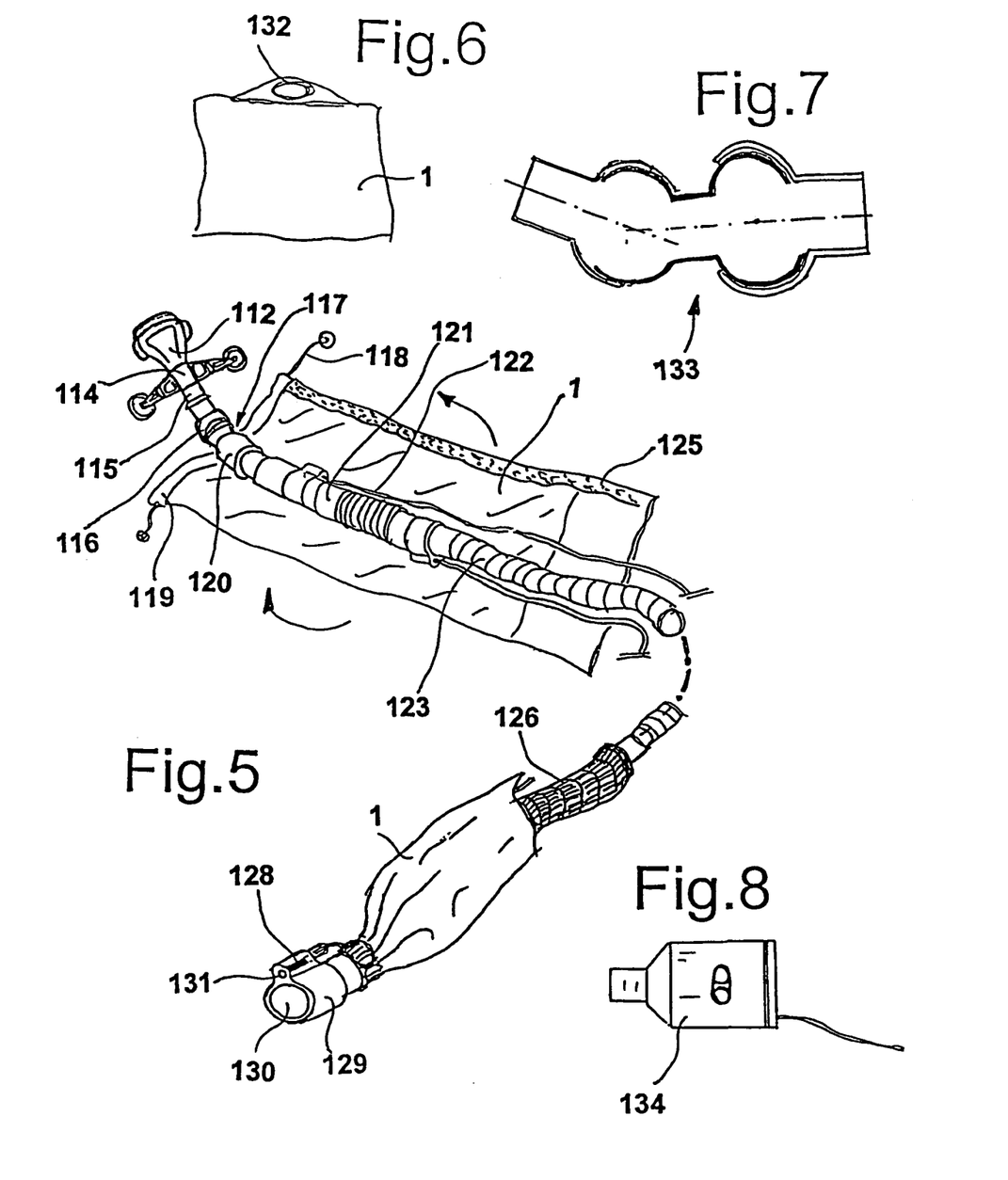
FIG. 5 shows a perspective sketch for elucidating a further embodiment of a respiratory gas tube arrangement.
FIG. 6 shows a sketch of a portion of the sheathing body, here with eye portions for suspending the sheathing body.
FIG. 7 shows a sketch for elucidating an articulated insert which can be inserted section-wise into the sheathing body.
FIG. 8 shows a sketch of a blower means (CPAP pressure source), in the form of a cartridge, for insertion into the sheathing body.

FIG. 5 shows a further embodiment of the respiratory gas tube arrangement, formed in connection with the sheathing body 1, including breathing mask 112.

The breathing mask 112 is connected to an articulated piece 116 through the intermediary of a washing valve 115 integrated into a forehead spacer 114. Formed in the region of the articulated piece 116 is a circumferential groove 117 in which a front collar region 119 of the sheathing body 1 can be fixed by means of a lashing tape 118.

The articulated piece 116 is adjoined by a respiratory gas flowrate measuring member 120, which can be connected to a respiratory gas pressure source, such as a CPAP device, via a measuring line (not visible here).

The respiratory gas tube apparatus additionally comprises a respiratory gas humidifier 121 which can be connected to a water source via a humidification line 122. The respiratory gas humidifier 121 is in the form of a flexible tube piece and is disposed between the breathing mask 112 and the main part of the respiratory gas tube 23.

In the region of the respiratory gas humidifier 121, the sheathing body 1 is provided with a super-insulating foil, with the result that a great thermal insulation effect is achieved in the region of the humidifier. This makes it possible for the heat required for evaporating the humidification water to be drawn exclusively—or at least predominantly—from the respiratory air.

In the closed position, the sheathing body 1 surrounds the respiratory gas tube, composed of a plurality of modules, in the manner of a tube and closes off the respiratory gas tube to the outside. The sheathing body 1 is provided with a VEL-CRO™ (hook and loop) fastener tape 125 in the example embodiment shown.

The respiratory gas tube further comprises a tube silencer 126, which, in this case, has a length of between approximately 80 and 120 cm and which permits the further absorption of any noises from a respiratory gas pressure source. In the embodiment shown here, said silencer 126, too, is surrounded by the sheathing body 1.

A heating means is integrated into the sheathing body 1. The power supply to said heating means is by means of contact elements 128 which are integrated into a connector 129. The connector 129 comprises a respiratory-gas passage cross-section 130 as well as a pressure measuring tube connection cross-section 131.

FIG. 6 shows a portion of the sheathing body 1 which is here provided with an eye 132 by means of which the sheathing body 1 can be suspended.

FIG. 7 shows an articulated members element 133 which can be inserted into the sheathing body 1 coaxially with the respiratory gas tube. The articulated members element 133 comprises a multiplicity of articulated members which are coupled together with such a tight fit that the respiratory gas tube arrangement can be bent into a desired form.

FIG. 8 shows a blower means 134, the outer dimensions of which are such that said blower means can likewise be inserted into the sheathing body 1. This makes it possible to create a CPAP apparatus which is spiral or wavy in form and which is adapted in modular fashion to the respective user.

What is claimed is:

1. Respiratory gas tube arrangement for supplying a respiratory gas to a breathing mask with a flexible tube, comprising:
   a flexible sheathing body adapted to be removably attached to the flexible tube so as to surround the flexible tube and extend along the flexible tube in use;
   a heater provided to the sheathing body; and
   a connector adapted to be provided to an end of the tube and adapted to engage a socket of a gas delivery device, the connector including a first portion that provides a respiratory gas passage and a second portion that provides integrated contact elements adapted to be engaged with a power supply provided to the socket of the gas delivery device by which power is supplied to the heater,
   wherein the gas passage and contact elements are arranged on the connector such that both an electric and pneumatic connection is provided when the connector is connected to the socket of the gas delivery device.

2. Respiratory gas tube arrangement according to claim 1, wherein the flexible sheathing body is formed of a heat-insulating material.

3. Respiratory gas tube arrangement according to claim 1 wherein the flexible sheathing body is formed of a fleece material.

4. Respiratory gas tube arrangement according to claim 1, wherein the flexible sheathing body comprises a plurality of material layers.

5. Respiratory gas tube arrangement according to claim 1, wherein the flexible sheathing body is provided in the region of at least one end with a closure device.

6. Respiratory gas tube arrangement according to claim 5, wherein the closure device is formed of a lashing device or a hook and loop fastener.

7. Respiratory gas tube arrangement according to claim 1, wherein the flexible sheathing body is split in the longitudinal direction.

8. Respiratory gas tube arrangement according to claim 7, wherein the flexible sheathing body comprises a hook and loop fastener extending along a side edge.

9. Respiratory gas tube arrangement according to claim 1, wherein each contact element extends generally parallel to a longitudinal axis of the gas passage.

10. Respiratory gas tube arrangement according to claim 1, wherein each contact element is provided within the second portion.

11. Respiratory gas tube arrangement according to claim 1, wherein the first portion is tubular and the second portion extends outwardly from the first portion.

12. Device for supplying a respiratory gas to a patient, comprising:
    a delivery device adapted to deliver the respiratory gas;
    a breathing mask;
    a flexible tube adapted to couple the breathing mask to the delivery device;
    a flexible sheathing body removably attached to the flexible tube, said flexible sheathing body surrounding the flexible tube and extending from the breathing mask to the delivery device;
    a heater provided to the sheathing body; and
    a connector provided to an end of the tube, the connector including a first portion that provides a respiratory gas passage and a second portion that provides integrated contact elements by which power is supplied to the heater,
    wherein the delivery device includes a socket adapted to receive the connector, the socket providing a gas outlet to deliver the respiratory gas to the gas passage and a power supply to engage the contact elements for supplying power to the heater, and the socket and connector are arranged such that both an electric and pneumatic connection is provided when the connector is connected to the socket of the delivery device.

13. Device according to claim 12, wherein the heater is integrated into the flexible sheathing body.

14. Device according to claim 12, wherein the heater includes a heating foil.

15. Device according to claim 12, wherein each contact element extends generally parallel to a longitudinal axis of the gas passage.

16. Device according to claim 12, wherein each contact element is provided within the second portion.

17. Device according to claim 12, wherein the first portion is tubular and the second portion extends outwardly from the first portion.

* * * * *